United States Patent
Kim et al.

(10) Patent No.: US 9,233,343 B2
(45) Date of Patent: Jan. 12, 2016

(54) CARBON DIOXIDE SEPARATION MEMBRANE COMPRISING POROUS HOLLOW TITANIUM DIOXIDE NANOPARTICLE AND MANUFACTURING METHOD THEREOF

(71) Applicant: INDUSTRY-ACADEMIC COOPERATION FOUNDATION, YONSEI UNIVERSITY, Seoul (KR)

(72) Inventors: Jong-Hak Kim, Seoul (KR); Dong Kyu Roh, Seoul (KR); Sang Jin Kim, Seoul (KR); Won Seok Chi, Gyeonggi-do (KR); Sung Yeon Heo, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/669,660

(22) Filed: Mar. 26, 2015

(65) Prior Publication Data
US 2015/0273402 A1    Oct. 1, 2015

(30) Foreign Application Priority Data
Mar. 27, 2014    (KR) .................. 10-2014-0035989

(51) Int. Cl.
*B01D 53/22*    (2006.01)
*B01D 71/02*    (2006.01)
(Continued)

(52) U.S. Cl.
CPC .............. *B01D 71/024* (2013.01); *B01D 69/06* (2013.01); *B01D 71/30* (2013.01); *C07F 7/28* (2013.01); *B01D 2325/02* (2013.01); *B01D 2325/20* (2013.01)

(58) Field of Classification Search
CPC ...... B01D 69/06; B01D 71/02; B01D 71/024; B01D 71/027; B01D 71/028; B01D 71/30; B01D 2325/02; B01D 2325/20; C04B 2235/3232; C04B 2235/3234; C04B 2235/3236; C04B 2235/3237; C07F 7/28
See application file for complete search history.

(56) References Cited

U.S. PATENT DOCUMENTS

| 3,542,596 A | * | 11/1970 | Arrance | .............. | H01M 2/1613 |
| | | | | | 429/145 |
| 4,762,543 A | | 8/1988 | Pantermuehl et al. | | |

(Continued)

FOREIGN PATENT DOCUMENTS

KR    10-2013-0110427    10/2013

OTHER PUBLICATIONS

Cong, Hailin, et al., "Aminosilane Cross-linked PEG/PEPEG/PPEPG Membranes for CO2/N2 and CO2/H2 Separation," Ind. Eng. Chem. Res., 2010, vol. 49, pp. 9363-9369.

*Primary Examiner* — Jason M Greene
*Assistant Examiner* — Anthony Shumate
(74) *Attorney, Agent, or Firm* — Duane Morris LLP; J. Rodman Steele, Jr.; Gregory M. Lefkowitz (57) ABSTRACT

Provided is a carbon dioxide separation membrane. The carbon dioxide separation membrane includes porous hollow titanium dioxide nanoparticles whose surfaces are modified with aminosilane having high affinity with carbon dioxide and a crosslinkable functional group. The carbon dioxide separation membrane provides both improved selectivity and improved permeability. In addition, the carbon dioxide separation membrane includes a copolymer matrix having excellent mechanical properties. Thus, it is possible to provide a carbon dioxide separation membrane having excellent selectivity and permeability as well as improved physical strength, chemical stability and temperature resistance.

12 Claims, 7 Drawing Sheets

(51) Int. Cl.
   *B01D 69/06* (2006.01)
   *B01D 71/30* (2006.01)
   *C07F 7/28* (2006.01)

(56) References Cited

U.S. PATENT DOCUMENTS

| | | | |
|---|---|---|---|
| 5,049,167 A | 9/1991 | Castro et al. | |
| 5,104,425 A * | 4/1992 | Rao | B01D 53/33 55/DIG. 5 |
| 5,585,011 A * | 12/1996 | Saaski | B01D 61/18 210/490 |
| 6,165,605 A * | 12/2000 | Fujita | B22D 19/16 428/311.51 |
| 6,649,255 B1 * | 11/2003 | Fain, Sr. | B01D 53/228 210/500.25 |
| 6,916,454 B2 * | 7/2005 | Alvin | B01D 53/22 422/211 |
| 7,019,209 B2 * | 3/2006 | Spivack | H01G 9/2031 136/252 |
| 7,094,733 B2 * | 8/2006 | Laney | B41M 5/41 503/227 |
| 7,101,819 B2 * | 9/2006 | Rosenflanz | C03B 19/06 428/426 |
| 7,846,496 B2 * | 12/2010 | Liu | B01D 67/0079 427/216 |
| 8,877,286 B2 * | 11/2014 | Kuniyasu | G02B 1/04 427/162 |
| 8,968,825 B1 * | 3/2015 | Kawde | G01N 27/308 427/113 |
| 9,023,454 B2 * | 5/2015 | Kikuchi | B01D 53/9413 422/180 |
| 2002/0141919 A1 * | 10/2002 | Alvin | B01D 53/22 422/211 |
| 2004/0112420 A1 * | 6/2004 | Spivack | H01G 9/2031 136/256 |
| 2005/0112302 A1 * | 5/2005 | Laney | B41M 5/506 428/32.31 |
| 2005/0112352 A1 * | 5/2005 | Laney | B41M 5/506 428/304.4 |
| 2005/0161849 A1 * | 7/2005 | Ohno | B22F 3/11 264/43 |
| 2005/0187104 A1 * | 8/2005 | Laney | B41M 5/41 503/227 |
| 2006/0154021 A1 * | 7/2006 | Ohno | B22F 3/11 428/116 |
| 2007/0249736 A1 * | 10/2007 | Watanabe | B41M 5/5218 516/81 |
| 2011/0300718 A1 * | 12/2011 | Yan | B01D 67/0041 438/782 |
| 2012/0237673 A1 * | 9/2012 | Kuniyasu | G02B 1/04 427/162 |
| 2015/0049458 A1 * | 2/2015 | Van Bommel | F21V 9/08 362/84 |
| 2015/0053554 A1 * | 2/2015 | Kawde | G01N 27/308 200/400 |
| 2015/0053611 A1 * | 2/2015 | Wang | B01D 71/64 210/500.23 |
| 2015/0223938 A1 * | 8/2015 | Tiainen | A61L 27/06 623/23.51 |

* cited by examiner

CARBON DIOXIDE SEPARATION MEMBRANE COMPRISING POROUS HOLLOW TITANIUM DIOXIDE NANOPARTICLE AND MANUFACTURING METHOD THEREOF

CROSS-REFERENCE TO RELATED APPLICATIONS

This application claims priority under 35 U.S.C. §119 to Korean Patent Application No. 10-2014-0035989 filed on Mar. 27, 2014 in the Korean Intellectual Property Office, the disclosure of which is incorporated herein by reference in its entirety.

TECHNICAL FIELD

The following disclosure relates to a carbon dioxide separation membrane including porous hollow titanium dioxide nanoparticles. More particularly, the following disclosure relates to a carbon dioxide separation membrane including porous hollow titanium dioxide nanoparticles whose surfaces are modified with aminosilane and a crosslinkable functional group to provide excellent selectivity and permeability to carbon dioxide, and a method for efficiently producing the same.

BACKGROUND

Use of petroleum as a main energy source has generated air pollutants and green gas, resulting in recent severe environmental problems. To solve these, Kyoto Protocol was signed internationally for the purpose of regulation of carbon dioxide, a typical global warming material. Then, Korea has been included in the countries subjected to such regulation since 2013.

Under these circumstances, many attentions have been given to separation technologies for carbon dioxide. Main separation technologies for carbon dioxide that have been developed to date include pressure swing adsorption, water scrubbing, methanol scrubbing, polyethylene glycol scrubbing, membrane separation, cryogenic liquefaction, etc.

Membrane separation is a gas separation method using a separation membrane to allow a specific ingredient to permeate therethrough selectively. Such gas separation using a separation membrane performs gas separation through dissolution and diffusion, involves no phase change, and requires low energy consumption and a small area for installation to facilitate control and maintenance. By virtue of such advantages, many attentions have been given to membrane separation. In such a membrane separation method, a polymeric membrane has been used frequently. A commercially available separation membrane for carbon dioxide has a problem of trade-off between selectivity and permeability, because permeability is low when selectivity is high and selectivity is low when permeability is high, and shows disadvantages of low physical strength, chemical stability and temperature resistance.

Various polymeric composite membranes have been developed to overcome such problems. For example, a known technological process uses a polymeric separation membrane. However, the technological process requires maintenance of low temperature and provides low selectivity to carbon dioxide, and thus is not amenable to commercialization (Patent Document 1).

Meanwhile, it is known that a method including interfacial polymerization of polyimide onto a polymeric composite membrane increases carbon dioxide/hydrogen selectivity. However, the above method does not provide permeability and selectivity sufficient for commercialization (Patent Document 2).

REFERENCES

Patent Documents

Patent Document 1: U.S. Pat. No. 4,762,543
Patent Document 2: U.S. Pat. No. 5,049,167

SUMMARY

An embodiment of the present disclosure is directed to providing a carbon dioxide separation membrane including porous hollow titanium dioxide nanoparticles, which has improved permeability and selectivity by virtue of surface modification of the porous hollow titanium dioxide nanoparticles with aminosilane having high affinity to carbon dioxide and a crosslinkable functional group capable of controlling the surface pore size of nanoparticles. Another embodiment of the present disclosure is directed to providing a method for preparing the carbon dioxide separation membrane.

In one aspect, there is provided a carbon dioxide separation membrane including porous hollow titanium dioxide nanoparticles and a copolymer matrix.

The porous hollow titanium dioxide nanoparticles are surface modified with aminosilane and a crosslinkable functional group, wherein the crosslinkable functional group is positioned at the end of aminosilane.

The aminosilane is at least one selected from the group consisting of 3-aminopropyltriethoxysilane, N-(2-aminoethyl)-3-aminopropyltrimethoxysilane and N-(2-aminoethyl)-3-aminopropylmethyldiethoxysilane.

The crosslinkable functional group is any one selected from the group consisting of polyethylene glycol diglycidyl ether, epichlorohydrin, methylglycidyl ether, phenyl glycidyl ether, lauryl alcohol glycidyl ether, ethylene glycol dimethacrylate, 1,4-butanediol diglycidyl ether and ethylene glycol diglycidyl ether.

According to an embodiment, the porous hollow titanium dioxide nanoparticles may have an outer diameter of 200-350 nm and a density of 1.0-3.0 g/cm$^3$.

According to another embodiment, the porous hollow titanium dioxide nanoparticles may have a surface pore size of 3-15 nm and a specific surface area of 25-35 m$^2$/g.

According to still another embodiment, the carbon dioxide separation membrane may have a carbon dioxide permeability of 80-100 barren and a carbon dioxide selectivity of 40-50.

According to still another embodiment, the surface modified porous hollow titanium dioxide nanoparticles may be incorporated in an amount of 2-99 wt % based on the total weight of the copolymer.

The copolymer matrix is a polymer having a halogenated polymer backbone to which a hydrophilic monomer is grafted, wherein the halogenated polymer is selected from the group consisting of polyvinylidene fluoride-co-chlorotrifluoroethylene, polyvinyl chloride, polychlorotrifluoroethylene, polydichlorodifluoromethane, polyvinylidene dichloride and a copolymer thereof, and the hydrophilic monomer is selected from the group consisting of polyoxyethylene (meth)acrylate, poly(ethylene glycol) methyl ether (meth)acrylate, hydroxyethyl (meth)acrylate, hydrolyzed tert-butyl (meth)acrylate, acrylamide, N-vinylpyrrolidone, aminostyrene, styrene sulfonic acid, methylpropene sulfonic acid, sulfopropyl (meth)acrylate, sulfoethyl (meth)acrylate and sulfobutyl (meth)acrylate.

In another aspect, there is provided a method for producing porous hollow titanium dioxide nanoparticles for use in a carbon dioxide separation membrane, including the steps of:

I) carrying out hydrothermal synthesis of a mixture containing a titanium precursor and polyethylene glycol to obtain porous hollow titanium dioxide nanoparticles, II) dissolving the porous hollow titanium dioxide nanoparticles and aminosilane into a solvent and treating the surfaces of porous hollow titanium dioxide nanoparticles with aminosilane, and III) allowing the porous hollow titanium dioxide nanoparticles whose surfaces are modified with aminosilane to react with a crosslinkable functional group.

According to an embodiment, step I) may be carried out at 100-200° C. for 5-20 hours.

According to another embodiment, the titanium precursor may be potassium titanium oxide oxalate dihydrate (PTO).

According to still another embodiment, step II) and/or step III) may be carried out at 40-100° C. for 1-10 hours.

According to still another embodiment, the solvent may be any one selected from the group consisting of tetrahydrofuran, N-methylpyrrolidone, dimethylformaldehyde, dimethylsulfoxide, alcohols and a mixture thereof.

According to still another embodiment, the crosslinkable functional group may be any one selected from the group consisting of polyethylene glycol diglycidyl ether, epichlorohydrin, methylglycidyl ether, phenyl glycidyl ether, lauryl alcohol glycidyl ether, ethylene glycol dimethacrylate, 1,4-butanediol diglycidyl ether and ethylene glycol diglycidyl ether.

In still another aspect, there is provided a method for producing a carbon dioxide separation membrane, including dissolving the porous hollow titanium dioxide nanoparticles and a copolymer into a solvent, and subjecting the resultant mixture to ultrasonication or physical agitation.

According to the present disclosure, since the surfaces of porous hollow titanium dioxide nanoparticles are bound with aminosilane having high affinity to carbon dioxide and a crosslinkable functional group for controlling the surface pore size of nanoparticles, it is possible to improve carbon dioxide selectivity and permeability at the same time. In addition, by virtue of the presence of a copolymer having excellent physical properties, it is possible to obtain a carbon dioxide separation membrane having not only improved carbon dioxide selectivity and permeability but also improved physical strength, chemical stability and temperature resistance.

DETAILED DESCRIPTION OF EMBODIMENTS

Hereinafter, various aspects and exemplary embodiments of the present disclosure are described in further detail.

Permeation of gas through a separation membrane may be represented by the following formula:

$$q = P \cdot A \cdot \Delta p / L$$

wherein q is an amount ($cm^3/s$) of gas passing through the membrane per unit time, P represents the gas permeability of a separation membrane expressed in the unit of barrer [$(cm^3 \cdot cm)/(s \cdot cm^2 \cdot mmHg)$], A is the surface area ($cm^2$) of a separation membrane, p is a difference in partial pressure of gas between the inner part of separation membrane and the outer part thereof, and L is the thickness of a separation membrane.

In addition, 'selectivity' refers to selectivity between $CO_2$ and the other gases ($N_2$, $CH_4$, etc.). For example, in the case of carbon dioxide/nitrogen ($CO_2/N_2$) selectivity, it means the ratio of selection of carbon dioxide ($CO_2$) gas as compared to that of nitrogen ($N_2$).

In one aspect, there is provided a carbon dioxide separation membrane including porous hollow titanium dioxide nanoparticles, wherein the porous hollow titanium dioxide nanoparticles are surface-modified with aminosilane and a crosslinkable functional group, and the crosslinkable functional group is positioned at the end of aminosilane.

According to the related art, carbon dioxide separation membranes have problems in that their permeability and selectivity are in inverse proportion with each other because permeability is low when selectivity is high and permeability is high when selectivity is low. Therefore, there is provided a carbon dioxide separation membrane obtained by using porous hollow titanium dioxide nanoparticles whose inner parts are vacant. Such a carbon dioxide separation membrane shows increased permeability through Knudsen diffusion. In addition, the porous hollow titanium dioxide nanoparticles are surface-modified with aminosilane and a crosslinkable functional group, thereby improving selectivity to carbon dioxide while preventing degradation of permeability.

More particularly, the porous hollow titanium dioxide nanoparticles are surface treated with aminosilane having high affinity to carbon dioxide to increase the solubility of carbon dioxide, resulting in improvement of selectivity. In addition, the porous hollow titanium dioxide nanoparticles are bound with a crosslinkable functional group so that the pore size of porous hollow titanium dioxide nanoparticles may be controlled. Thus, indiscriminate permeation of nitrogen having a large dynamic diameter may be prevented and nitrogen permeability may be inhibited, resulting in improvement of selectivity.

The carbon dioxide separation membrane includes a copolymer matrix. Preferably, the copolymer matrix has a halogenated polymer backbone as a hydrophobic region and a hydrophilic monomer is grafted to the backbone.

The halogenated polymer may include, but is not limited to, polyvinylidene fluoride-co-chlorotrifluoroethylene, polyvinyl chloride, polychlorotrifluoroethylene, polydichlorodifluoromethane, polyvinylidene dichloride and a copolymer thereof.

The hydrophilic monomer may include, but is not limited to, polyoxyethylene (meth)acrylate, poly(ethylene glycol) methyl ether (meth)acrylate, hydroxyethyl (meth)acrylate, hydrolyzed tert-butyl (meth)acrylate, acrylamide, N-vinylpyrrolidone, aminostyrene, styrene sulfonic acid, methylpropene sulfonic add, sulfopropyl (meth)acrylate, sulfoethyl (meth)acrylate, sulfobutyl (meth)acrylate or a combination thereof.

More preferably, the halogenated polymer may be polyvinyl chloride and the hydrophilic monomer may be poly(ethylene glycol) methyl ether (meth)acrylate.

More particularly, the copolymer matrix may be represented by the following Chemical Formula 1:

[Chemical Formula 1]

The copolymer matrix is hydrophobic, and has a microphase separation structure including a halogenated polymer having excellent mechanical properties and a hydrophilic monomer grafted to the halogenated polymer and having excellent selective separatability to carbon dioxide. Thus, when the copolymer matrix is incorporated to a carbon dioxide separation membrane, it is possible to obtain excellent selective separatability to carbon dioxide and improved physical strength, chemical stability and temperature resistance.

In addition, the copolymer matrix has high affinity with the porous hollow titanium dioxide nanoparticles so that the nanoparticles may be dispersed homogeneously in the matrix. Thus, a carbon dioxide separation membrane including the copolymer matrix has lithe gaps such as cracks, defects and pores, and thus prevents indiscriminate permeation of gas molecules and degradation of selectivity.

The aminosilane may be at least one selected from the group consisting of 3-aminopropyltriethoxysilane, N-(2-aminoethyl)-3-aminopropyltrimethoxysilane and N-(2-aminoethyl)-3-aminopropylmethyldiethoxysilane.

The crosslinkable functional group may be any one selected from the group consisting of polyethylene glycol diglycidyl ether, epichlorohydrin, methylglycidyl ether, phenyl glycidyl ether, lauryl alcohol glycidyl ether, ethylene glycol dimethacrylate, 1,4-butanediol diglycidyl ether and ethylene glycol diglycidyl ether.

The porous hollow titanium dioxide nanoparticles may have an outer diameter of 210-400 nm, an inner diameter of 200-350 nm, and a shell thickness of 20-40 nm. The surfaces of porous hollow titanium dioxide nanoparticles enable rapid diffusion of gas molecules while their hollow inner structures allow the gas molecules passing through the surfaces to permeate therethrough with no structural hindrance. In this manner, it is possible to improve the permeability of gas molecules.

The porous hollow titanium dioxide nanoparticles may have a density of 1.0-3.0 g/cm$^3$. Such a density value is lower than the density of non-surface modified porous hollow titanium dioxide nanoparticles (4-5 g/cm$^3$) and is not significantly different from the density of a copolymer matrix (1-3 g/m$^3$). In this manner, it is possible to increase the dispersibility upon mixing the porous hollow titanium dioxide nanoparticles with the copolymer matrix.

The porous hollow titanium dioxide nanoparticles may have a pore size of 3-15 nm. Such a pore size is within a specific range selected to prevent indiscriminate permeation of nitrogen having a large dynamic diameter and to allow permeation of carbon dioxide selectively.

The porous hollow titanium dioxide nanoparticles may have a specific surface area of 25-35 m$^2$/g.

The carbon dioxide separation membrane may have a carbon dioxide permeability of 80-100 barrer and a carbon dioxide selectivity of 40-50. As can be demonstrated by the test results described hereinafter, such permeability and selectivity are significantly improved as compared to a carbon dioxide separation membrane including a copolymer matrix alone according to the related art.

The carbon dioxide separation membrane may include 2-99 wt % of the porous hollow titanium dioxide nanoparticles based on the total weight of copolymer matrix.

In another aspect, there is provided a method for producing porous hollow titanium dioxide nanoparticles for use in a carbon dioxide separation membrane, including the steps of:

I) carrying out hydrothermal synthesis of a mixture containing a titanium precursor and polyethylene glycol to obtain non-surface modified porous hollow titanium dioxide nanoparticles, II) dissolving the non-surface modified porous hollow titanium dioxide nanoparticles and aminosilane into a solvent and treating the surfaces of porous hollow titanium dioxide nanoparticles with aminosilane, and III) allowing the porous hollow titanium dioxide nanoparticles whose surfaces are modified with aminosilane to react with a crosslinkable functional group.

In step I), a hydrothermal reaction may be carried out at 100-200° C. for 5-20 hours. Step I) is intended to obtain non-surface modified porous hollow titanium dioxide nanoparticles by using the principle of Ostwald ripening. Particularly, small particles are formed tightly inside the nanoparticles and grown from the inside to the outside toward the shells. Herein, a titanium precursor is capped with polyethylene glycol to inhibit the hydrothermal reaction rate and to control the crystal growth rate, thereby providing non-surface modified porous hollow titanium dioxide nanoparticles.

The titanium precursor may be potassium titanium oxide oxalate dihydrate (PTO).

After Step I), the method may further include a step of carrying out heat treatment at 400-600° C. for 10-50 minutes. This step is intended to remove the organic materials remaining in the non-surface modified porous hollow titanium dioxide nanoparticles.

Step II) and/or step III) may be carried out at 40-100° C. for 1-10 hours.

The aminosilane may be at least one selected from the group consisting of 3-aminopropyltriethoxysilane, N-(2-aminoethyl)-3-aminopropyltrimethoxysilane and N-(2-aminoethyl)-3-aminopropylmethyldiethoxysilane, and more preferably 3-aminopropyltriethoxysilane.

The solvent may be any one selected from the group consisting of tetrahydrofuran, N-methylpyrrolidone, dimethyl formaldehyde, dimethyl sulfoxide, alcohols and mixtures thereof.

The crosslinkable functional group may be any one selected from the group consisting of polyethylene glycol diglycidyl ether, epichlorohydrin, methylglycidyl ether, phenyl glycidyl ether, lauryl alcohol glycidyl ether, ethylene glycol dimethacrylate, 1,4-butanediol diglycidyl ether and ethylene glycol diglycidyl ether.

The porous hollow titanium dioxide nanoparticles for use in a carbon dioxide separation membrane obtained by the above method may have a specific surface area of 25-35 m²/g and a density of 1.0-3.0 g/cm³.

In addition, the porous hollow titanium dioxide nanoparticles for a carbon dioxide separation membrane obtained by the above method may have an outer diameter of 210-400 nm, an inner diameter of 200-350 nm and a shell thickness of 20-40 nm.

In still another aspect, there is provided a method for producing a carbon dioxide separation membrane, including dissolving the porous hollow titanium dioxide nanoparticles and a copolymer into a solvent, and subjecting the resultant mixture to ultrasonication or physical agitation.

The examples and experiments will now be described. The following examples and experiments are for illustrative purposes only and not intended to limit the scope of this disclosure.

Preparation Example 1

Preparation of Porous Hollow Titanium Dioxide Nanoparticles (1) 0.266 g of potassium titanium oxide oxalate dihydrate (also referred to as PTO hereinafter) is introduced to 45 mL of ultrapure water (deionized (DI) water) and dissolved completely therein for 2 hours. Next, 22.5 mL of polyethylene glycol (also referred to as PEG hereinafter) is added thereto, followed by agitation, to obtain a first mixed solution. After the first mixed solution is further agitated for 30 minutes, it is allowed to react in an autoclave at 180° C. for 15 hours. After the completion of reaction, the precipitate is subjected to centrifugal separation to obtain non-surface modified porous hollow titanium dioxide nanoparticles (also referred to as MTHS hereinafter). The thus obtained non-surface modified porous hollow titanium dioxide nanoparticles are washed many times with water and ethanol, followed by drying. The drying is carried out in an oven at 50° C. overnight. Then, heat treatment is carried out at 500° C. for 30 minutes to remove the organic materials remaining in the resultant non-surface modified porous hollow titanium dioxide nanoparticles (MTHS). Herein, the non-surface modified porous hollow titanium dioxide nanoparticles are those having a porous hollow nano-spherical shape before surface modification.

(2) To modify the surfaces of the thus obtained MTHS, the following procedure is carried out.

First, 0.4 g of the thus obtained MTHS is dispersed into 90 mL of toluene and 6 mL of 3-aminopropyl triethoxysilane (also referred to as APS hereinafter) is added thereto to obtain a second mixed solution. The second mixed solution is allowed to react at 60° C. for 6 hours and subjected to centrifugal separation so that it is separated into the supernatant and pellets. Then, the supernatant is removed. The resultant product is washed with ethanol three times to remove the remaining unreacted 3-aminopropyl triethoxysilane, followed by drying, and then dried in an oven at 50° C. Further, the resultant product is cured at 120° C. for 2 hours to obtain porous hollow titanium dioxide nanoparticles surface modified with APS. The thus obtained porous hollow titanium dioxide nanoparticles whose surfaces are modified with APS is dispersed into 80 mL of toluene solution in which polyethyleneglycol diglycidyl ether (also referred to as PEGDE) is incorporated (10 v/v %), and allowed to react at 80° C. for 8 hours. After the completion of reaction, the precipitate is separated by centrifugal separation to obtain porous hollow titanium dioxide nanoparticles whose surfaces are modified with APS and PEGDE. The thus obtained porous hollow titanium dioxide nanoparticles whose surfaces are modified with APS and PEGDE (also referred to as 'porous hollow titanium dioxide or f-MTHS') are washed with water three times to remove polyethyleneglycol diglycidyl ether remaining therein, followed by drying in an oven at 50° C. overnight.

Preparation Example 2

Preparation of Copolymer Matrix

First, 6 g of polyvinyl chloride (PVC) is dissolved completely into 50 mL of N-methypyrrolidone (NMP). Then, 24 mL of polyethylene glycol methyl ether methacryate, 0.10 g of CuCl and 0.24 mL of 1,1,4,7,10,10-hexamethyl triethylenetetramine (HMTETA) are added thereto to obtain a third mixed solution. The third mixed solution is allowed to react at 90° C. for 24 hours in an agitator, after nitrogen is introduced thereto over 30 minutes during the agitation. After the completion of reaction, methanol is added to the third mixed solution to cause precipitation, and the precipitate is filtered to recover PVC-g-POEM branched polymer as a copolymer matrix. Herein, the synthesis of copolymer matrix is based on atomic transfer radical polymerization (ATRP), which allows concentration onto the polymer backbone while maintaining a low concentration of free radicals and facilitates the control of process, thereby inhibiting generation of undesired side reactions. The method is one of the controlled free radical polymerization methods. In other words, undesired side reaction products, such as homopolymers and chain decomposition products are inhibited and removed to realize a grafting reaction capable of the synthesis of a copolymer matrix through a minimized single process. Herein, the PVC-g-POEM branched polymer has a ratio of PVC:POEM of 20:80 (wt %).

The copolymer matrix (PVC-g-POEM branched polymer) obtained as described above may be represented by the following Chemical Formula 1.

[Chemical Formula 1]

Examples 1-3

Production of Carbon Dioxide Separation Membrane

To produce a carbon dioxide separation membrane, the PVC-g-POEM branched polymer (Preparation Example 2) is dissolved into an adequate solvent, such as THF. Next, in a separate container, porous hollow titanium dioxide nanoparticles (Preparation Example 1, f-MTHS) are dispersed into an adequate solvent, such as THF, by using ultrasonication and physical agitation. The two solutions are mixed with each other, agitated sufficiently, poured to a petri dish and dried to obtain a carbon dioxide separation membrane. The carbon dioxide separation membrane is dried in a vacuum oven for 24 hours to remove the solvent completely therefrom.

Examples 1-3 include f-MTHS in an amount of 10, 20 and 30 wt %, respectively, based on the total weight of each carbon dioxide separation membrane.

Comparative Example 1

A carbon dioxide separation membrane is obtained in the same manner as Example 1, except that f-MTHS is not used.

Comparative Example 2

A carbon dioxide separation membrane is obtained in the same manner as Example 1, except that MTHS is used instead of f-MTHS.

Figure 1:
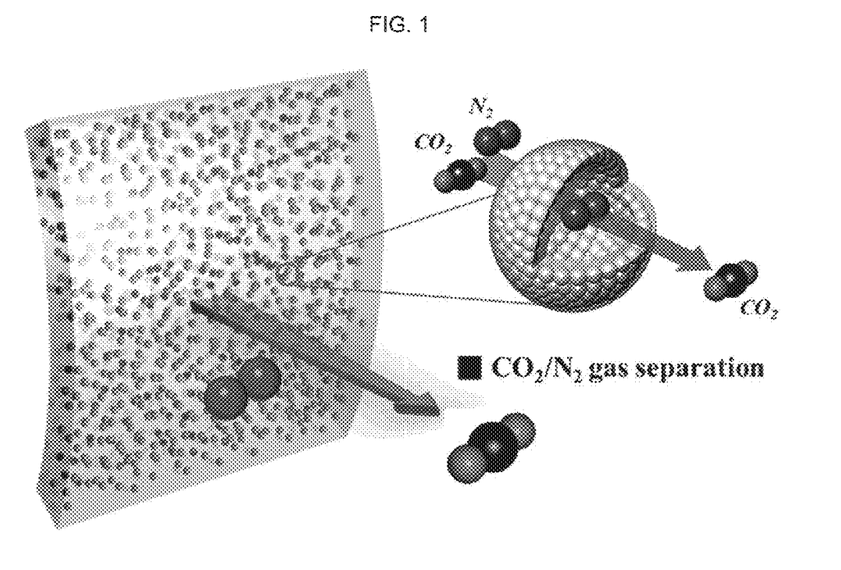
FIG. 1 is a schematic view illustrating the structure and operation mechanism of the carbon dioxide separation membrane according to an embodiment.
Figure 2:
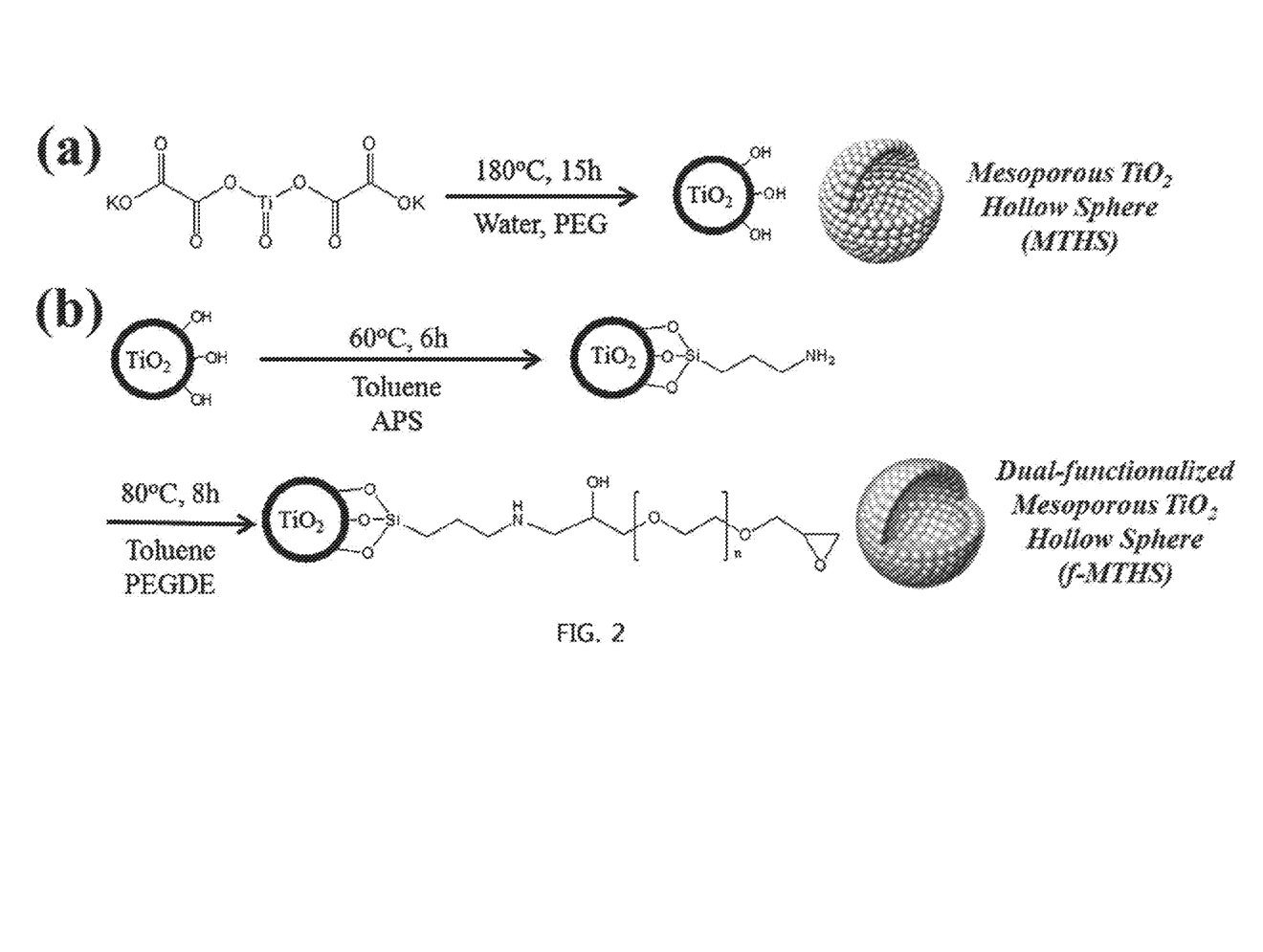
FIG. 2 shows a process for producing porous hollow titanium dioxide nanoparticles according to an embodiment.
Figure 3A:
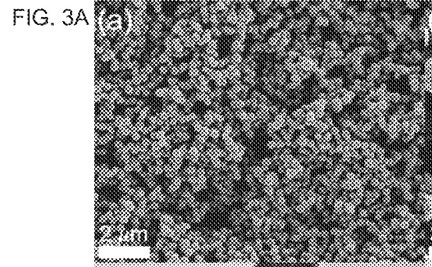
FIG. 3a and FIG. 3b are scanning electron microscopy (SEM) images of the porous hollow titanium dioxide nanoparticles obtained from Preparation Example 1.
Figure 3B:
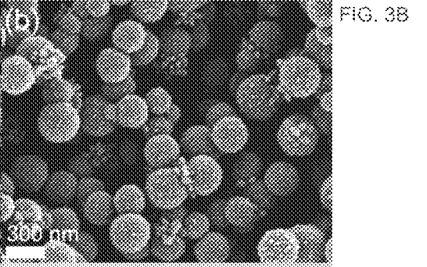
Figure 3C:
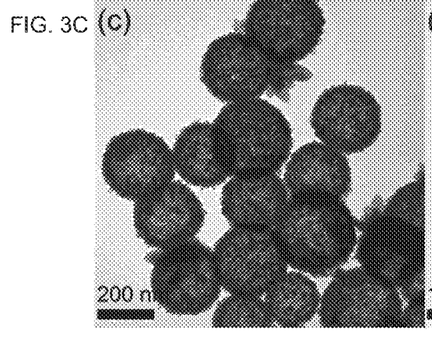
FIG. 3c and FIG. 3d are transmission electron microscopy (TEM) images of the porous hollow titanium dioxide nanoparticles obtained from Preparation Example 1.
Figure 3D:
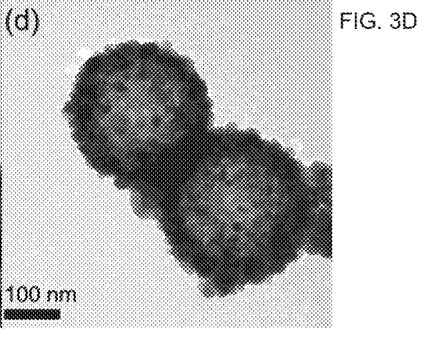

Test Example (1) FIG. 3a and FIG. 3b are scanning electron microscopy (SEM) images of the porous hollow titanium dioxide nanoparticles obtained from Preparation Example 1, and FIG. 3c and FIG. 3d are transmission electron microscopy (TEM) images of the porous hollow titanium dioxide nanoparticles obtained from Preparation Example 1.

Referring to the images, it can be seen that the porous hollow titanium dioxide nanoparticles obtained from Preparation Example 1 are porous hollow nanoparticles having a vacant inner part and micropores formed on the surfaces thereof.

In addition it is shown that porous hollow titanium dioxide nanoparticles (f-MTHS) obtained from Preparation Example 1 have an outer diameter of 280±30 nm, inner diameter of 250±30 nm and a shell thickness of 28±2 nm.

Figure 4:
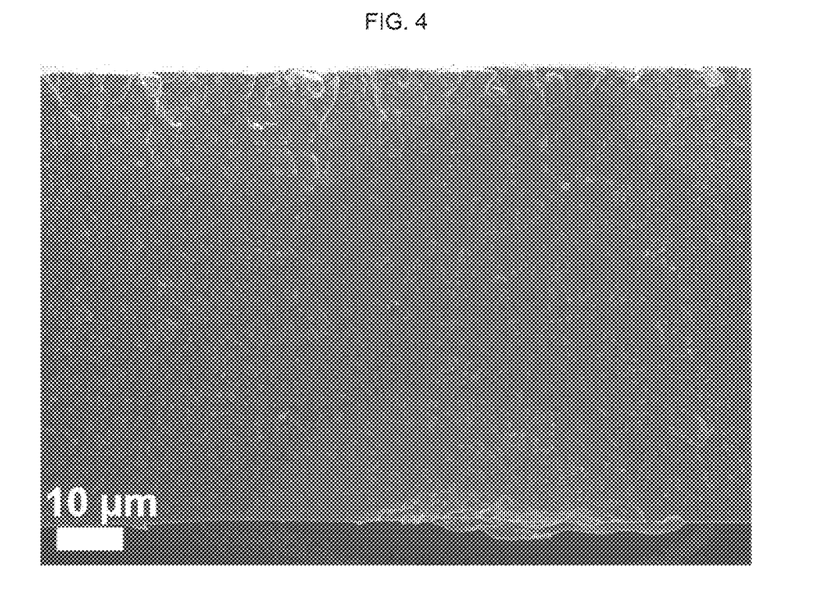
FIG. 4 is an SEM image of the carbon dioxide separation membrane obtained from Example 1.

(2) FIG. 4 is an SEM image of the carbon dioxide separation membrane obtained from Example 1.

Referring to the image, it can be seen that the carbon dioxide separation membrane obtained by using the porous hollow titanium dioxide nanoparticles (Preparation Example 1) and the copolymer matrix (Preparation Example 2) shows an insignificant difference in density as compared to the copolymer matrix, and is surface-modified with aminosilane having high affinity to the copolymer matrix and a crosslinkable functional group, and thus causes little gaps such as cracks or pores and is in a homogeneously mixed and distributed state.

As described above, the carbon dioxide separation membrane having a homogeneous distribution has little gaps therein, and thus prevents degradation of carbon dioxide selectivity, which, otherwise, occurs due to such gaps.

Figure 5:
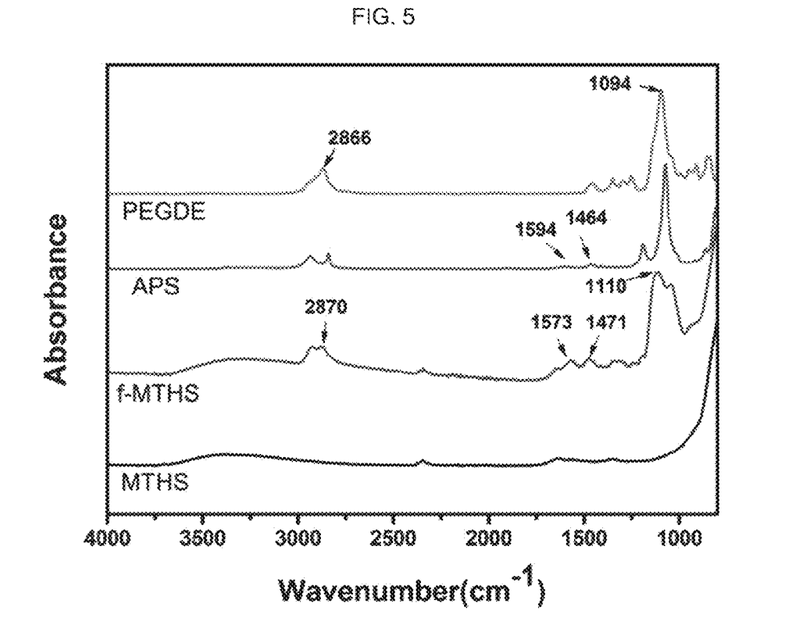
FIG. 5 is an FT-IR graph of the porous hollow titanium dioxide nanoparticles obtained from Preparation Example 1.

(3) FIG. 5 shows FT-IR spectrum of the porous hollow titanium dioxide nanoparticles obtained from Preparation Example 1.

It can be seen from the FT-IR spectrum of FIG. 5 that an N—H bending peak appears at 1573 cm$^{-1}$ and a C—N stretching peak appears at 1471 cm$^{-1}$. This suggests that APS is bound successfully to the surfaces of the porous hollow titanium dioxide nanoparticles obtained from Preparation Example 1.

In addition, a CH asymmetric stretching peak appears at 2870 cm$^{-1}$ and a C—O—C stretching movement peak appears at 1100 cm$^{-1}$, which suggests that PEGDE is positioned at the end of APS bound the surfaces of the porous hollow titanium dioxide nanoparticles obtained from Preparation Example 1.

Figure 6:
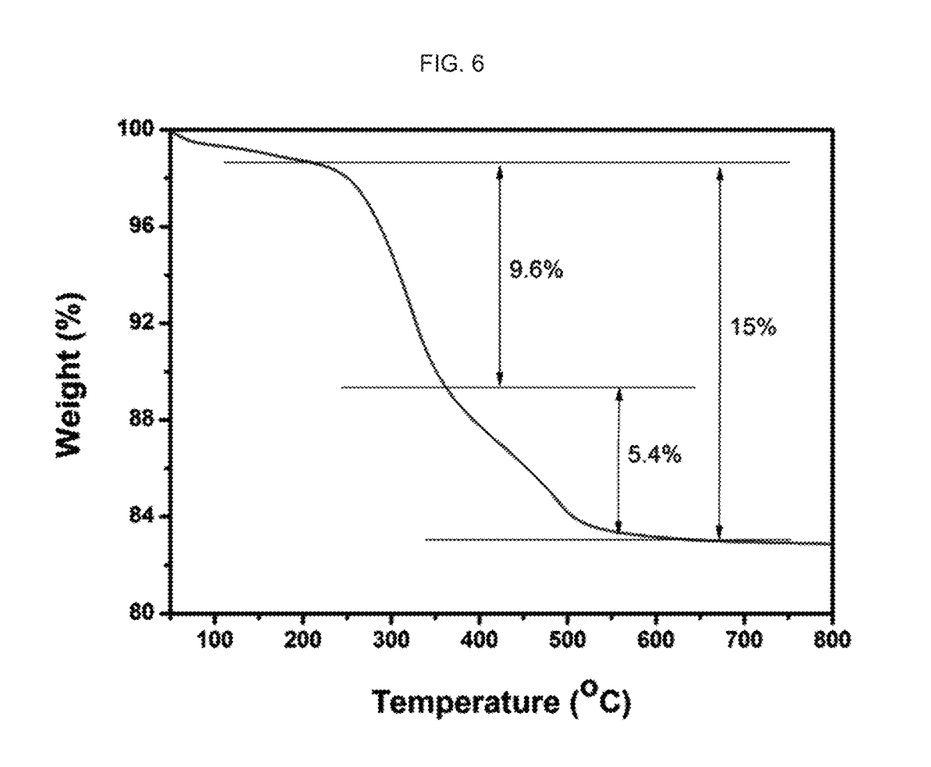
FIG. 6 is a thermogravimetric analysis (TGA) graph of the porous hollow titanium dioxide nanoparticles obtained from Preparation Example 1 for use in determination of the content of aminosilane and polyethylene glycol bound to the surfaces of the porous hollow titanium dioxide nanoparticles according to an embodiment.

(4) FIG. 6 is a thermogravimetric analysis (TGA) graph of the porous hollow titanium dioxide nanoparticles obtained from Preparation Example 1 for use in determination of the content of APS and PEGDE bound to the surfaces of the porous hollow titanium dioxide nanoparticles obtained from Preparation Example 1.

It can be seen from the graph that decomposition steps appear in two regions. More particularly, the porous hollow titanium dioxide nanoparticles obtained from Preparation Example 1 show a decrease in weight of about 9.6 wt % corresponding to the decomposition of PEGDE at 230-270° C. In addition, the nanoparticles show a decrease in weight of about 5.4 wt % corresponding to the decomposition of APS at 370-540° C. It can be seen from the above results that the total content of organic materials bound to the porous hollow titanium dioxide nanoparticles obtained from Preparation Example 1 is 15 wt %.

Figure 7:
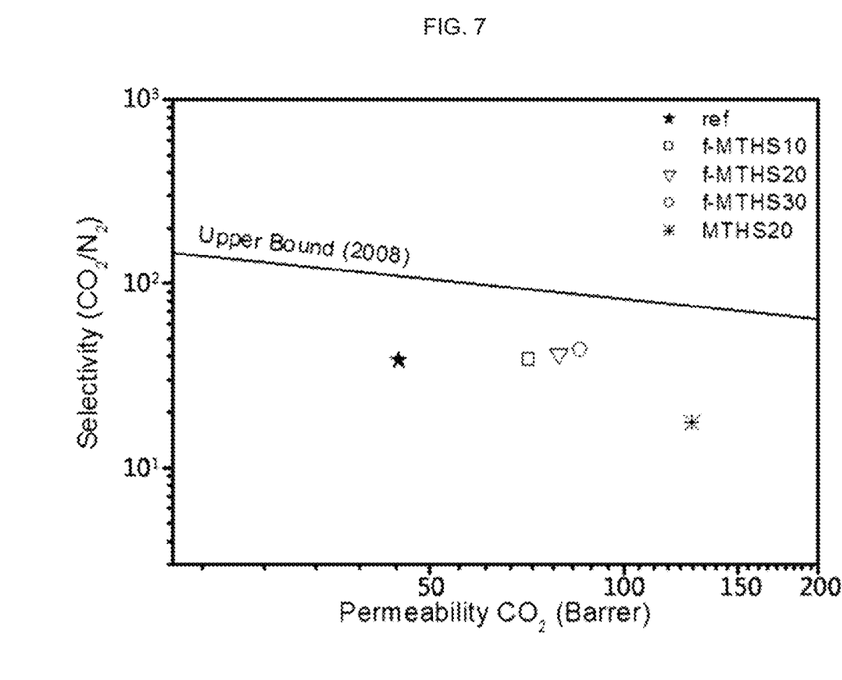
FIG. 7 is a graph illustrating $CO_2/N_2$ selectivity of each of the carbon dioxide separation membranes obtained from Examples 1-3 and Comparative Examples 1 and 2.
Figure 8:
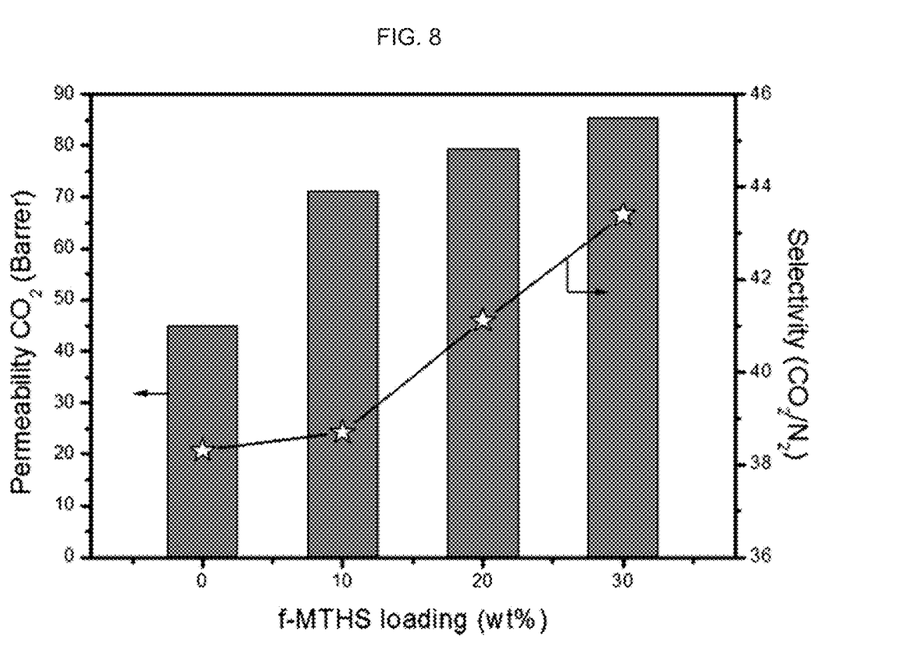
FIG. 8 is a graph illustrating the permeability and selectivity of each of the carbon dioxide separation membranes obtained from Examples 1-3 and Comparative Examples 1 and 2.

(5) FIG. 7 is a graph illustrating carbon dioxide/nitrogen selectivity of each of the carbon dioxide separation membranes obtained from Examples 1-3 and Comparative Examples 1 and 2. FIG. 8 is a graph illustrating the permeability and selectivity of each of the carbon dioxide separation membranes obtained from Examples 1-3 and Comparative Examples 1 and 2. The results are shown in the following Table 1.

TABLE 1

|  | MTHS (wt %) | f-MTHS (wt %) | P(CO$_2$) (Barrer) | P(N$_2$) (Barrer) | Selectivity (CO$_2$/N$_2$) |
|---|---|---|---|---|---|
| Ex. 1 | — | 10 | 71.18 | 1.84 | 38.7 |
| Ex. 2 | — | 20 | 79.33 | 1.93 | 41.1 |
| Ex. 3 | — | 30 | 85.41 | 1.97 | 43.4 |
| Comp. Ex. 1 | — | — | 44.81 | 1.17 | 38.3 |
| Comp. Ex. 2 | 20 | — | 127.35 | 7.18 | 17.7 |

FIG. 7, FIG. 8 and Table 1 show the results of separation of mixed gas containing pure carbon dioxide and nitrogen, as determined by using a time-lag method under the conditions of 800 mmHg and 35° C.

According to the results, in the case of the carbon dioxide separation membrane including the copolymer matrix alone according to Comparative Example 1, it provides a permeability of 44.81 and a selectivity of 38.3 after determination. Meanwhile, in the case of the carbon dioxide separation membrane including the non-surface modified porous hollow titanium dioxide nanoparticles (MTHS) according to Comparative Example 2, it provides a significantly increased carbon dioxide permeability of 127.35 barrer due to the Knudsen diffusion into the vacant inner part of MTHS. However, it provides a significantly decreased carbon dioxide/nitrogen selectivity of 17.7 due to the characteristics of Knudsen diffusion including an inverse proportional relationship with molecular weight and indiscriminate permeation of gases through the gaps caused by the weak interaction between MTHS particles and the copolymer matrix.

On the contrary, the carbon dioxide separation membrane according to Examples 3 provides a permeability of 85.41 barrer and a carbon dioxide/nitrogen selectivity of 43.4, which are significantly improved as compared to Comparative Examples 1 and 2.

Meanwhile, Comparative Example 2 shows a higher permeability as compared to Examples 1-3 but it shows a significant decrease in carbon dioxide/nitrogen selectivity at the same time. On the contrary, it should be noted that each of the carbon dioxide separation membranes according to Examples 1-3 shows a simultaneous increase in permeability and selectivity, and provides a permeability and selectivity improved significantly as compared to the conventional polymer separation membrane (Comparative Example 1).

The above results suggest that the organic materials bound to the surfaces of the porous hollow titanium dioxide nanoparticles according to the present disclosure improve the selectivity among gas molecules, while the organic chains block the pores present on the surfaces of the porous hollow titanium dioxide nanoparticles according to the present disclosure to prevent a significant increase in permeability. However, such blocking causes no gaps between the f-MTHS copolymer matrix and the nanoparticles, thereby preventing indiscriminate permeation of nitrogen and a decrease in carbon dioxide/nitrogen selectivity.

(6) The specific surface area and average pore size of the porous hollow titanium dioxide nanoparticles obtained from Preparation Example 1 and those of MTHS are calculated based on Brunauer-Emmett-Teller (BET) and Barrett-Joyner-Halenda (BJH). The porous hollow titanium dioxide nanoparticles obtained from Preparation Example 1 have a specific surface area of 29.3 $m^2/g$ and an average pore size of 6 nm. It is thought that this is because the pores are blocked due to PEGDE bound to the surfaces of the porous hollow titanium dioxide nanoparticles obtained from Preparation Example 1. Meanwhile, MTHS has a specific surface area of 45.9 $m^2/g$ and an average pore size of 18 nm.

In other words, since the non-surface modified porous hollow titanium dioxide nanoparticles have large-size pores on the surfaces thereof, they cause significant loss of selectivity in gas permeation, resulting in degradation of selectivity to carbon dioxide.

What is claimed is:

1. A carbon dioxide separation membrane comprising:
   porous hollow titanium dioxide nanoparticles whose surfaces are modified with aminosilane and a crosslinkable functional group; and
   a copolymer matrix.

2. The carbon dioxide separation membrane according to claim 1, wherein the crosslinkable functional group is any one selected from the group consisting of polyethylene glycol diglycidyl ether, epichlorohydrin, methylglycidyl ether, phenyl glycidyl ether, lauryl alcohol glycidyl ether, ethylene glycol dimethacrylate, 1,4-butanediol diglycidyl ether and ethylene glycol diglycidyl ether, and is positioned at the end of aminosilane.

3. The carbon dioxide separation membrane according to claim 1, wherein the aminosilane is at least one selected from the group consisting of 3-aminopropyltriethoxysilane, N-(2-aminoethyl)-3-aminopropyltrimethoxy silane and N-(2-aminoethyl)-3-aminopropylmethyldiethoxysilane.

4. The carbon dioxide separation membrane according to claim 1, wherein the copolymer matrix is a polymer having a halogenated polymer backbone to which a hydrophilic monomer is grafted,
   the halogenated polymer is selected from the group consisting of polyvinylidene fluoride-co-chlorotrifluoroethylene, polyvinyl chloride, polychlorotrifluoroethylene, polydichlorodifluoromethane, polyvinylidene dichloride and a copolymer thereof, and
   the hydrophilic monomer is selected from the group consisting of polyoxyethylene (meth)acrylate, poly(ethylene glycol) methyl ether meth)acrylate, hydroxyethyl (meth)acrylate, hydrolyzed tert-butyl (meth)acrylate, acrylamide, N-vinylpyrrolidone, aminostyrene, styrene sulfonic acid, methylpropene sulfonic acid, sulfopropyl (meth)acrylate, sulfoethyl (meth)acrylate and sulfobutyl (meth)acrylate.

5. The carbon dioxide separation membrane according to claim 1, which comprises the porous hollow titanium dioxide nanoparticles in an amount of 2-99 wt % based on the total weight of the copolymer matrix.

6. The carbon dioxide separation membrane according to claim 1, wherein the porous hollow titanium dioxide nanoparticles have an outer diameter of 50-800 nm, a pore size of 3-15 nm and a specific surface area of 25-35 $m^2/g$.

7. The carbon dioxide separation membrane according to claim 1, wherein the porous hollow titanium dioxide nanoparticles have a density of 1.0-3.0 $g/cm^3$.

8. The carbon dioxide separation membrane according to claim 1, wherein the porous hollow titanium dioxide nanoparticles have a carbon dioxide permeability of 80-1000 barrer and a carbon dioxide selectivity of 20-100.

9. A method for producing a carbon dioxide separation membrane, comprising the steps of:
   (a) forming porous hollow titanium dioxide nanoparticles whose surfaces are modified with aminosilane and a crosslinkable functional group, said forming comprising:
   I) carrying out hydrothermal synthesis of a mixture containing a titanium precursor and polyethylene glycol to obtain porous hollow titanium dioxide nanoparticles,
   II) dissolving the porous hollow titanium dioxide nanoparticles and aminosilane into a solvent and treating the surfaces of porous hollow titanium dioxide nanoparticles with aminosilane, and
   III) allowing the porous hollow titanium dioxide nanoparticles whose surfaces are modified with aminosilane to react with a crosslinkable functional group; and
   (b) forming a copolymer matrix including the porous hollow titanium dioxide nanoparticles whose surfaces are modified with aminosilane and a crosslinkable functional group to produce a carbon dioxide separation membrane.

10. The method for producing the carbon dioxide separation membrane according to claim 9, wherein step I) is carried out at 100-200° C. for 5-20 hours, and step II) and step III) are carried out at 40-100° C. for 1-10 hours.

11. The method for producing the carbon dioxide separation membrane according to claim 9, wherein the titanium precursor is potassium titanium oxide oxalate dihydrate (PTO).

12. The method for producing the carbon dioxide separation membrane according to claim 9, wherein the solvent is any one selected from the group consisting of tetrahydrofuran, N-methylpyrrolidone, dimethylformaldehyde, dimethylsulfoxide, alcohols and a mixture thereof.

* * * * *